(12) United States Patent
Riviere et al.

(10) Patent No.: US 10,161,915 B2
(45) Date of Patent: Dec. 25, 2018

(54) IN-SITU CONTACTLESS MONITORING OF PHOTOMASK PELLICLE DEGRADATION

(71) Applicant: GLOBALFOUNDRIES Inc., Grand Cayman (KY)

(72) Inventors: Remi Riviere, Dresden (DE); Arthur Hotzel, Dresden (DE)

(73) Assignee: GLOBALFOUNDRIES, Grand Cayman (KY)

( * ) Notice: Subject to any disclaimer, the term of this patent is extended or adjusted under 35 U.S.C. 154(b) by 402 days.

(21) Appl. No.: 14/932,372

(22) Filed: Nov. 4, 2015

(65) Prior Publication Data
US 2017/0122913 A1    May 4, 2017

(51) Int. Cl.
*G01N 29/46* (2006.01)
*G01N 29/24* (2006.01)
*G03F 1/62* (2012.01)
*G03F 1/84* (2012.01)
*G01N 29/11* (2006.01)
*G01N 29/34* (2006.01)

(52) U.S. Cl.
CPC ......... *G01N 29/2418* (2013.01); *G01N 29/11* (2013.01); *G01N 29/348* (2013.01); *G01N 29/46* (2013.01); *G03F 1/62* (2013.01); *G03F 1/84* (2013.01); *G01N 2291/015* (2013.01); *G01N 2291/2697* (2013.01)

(58) Field of Classification Search
CPC .. G01N 29/2418; G01N 29/11; G01N 29/348; G01N 29/46; G01N 2291/015; G01N 2291/2697; G03F 1/62; G03F 1/84
USPC ................................................. 73/655, 579
See application file for complete search history.

(56) References Cited

U.S. PATENT DOCUMENTS

| 4,610,541 A * | 9/1986 | Tanimoto | G01N 21/94 250/559.41 |
| 6,834,548 B1 * | 12/2004 | Hibbs | G01N 29/11 73/579 |
| 2011/0014577 A1 * | 1/2011 | Hashimoto | G01N 21/94 430/325 |
| 2013/0032174 A1 * | 2/2013 | Huang | B08B 5/00 134/19 |
| 2016/0274471 A1 * | 9/2016 | Lee | G03F 1/84 |

* cited by examiner

*Primary Examiner* — Helen Kwok
*Assistant Examiner* — Nashmiya Fayyaz
(74) *Attorney, Agent, or Firm* — Ditthavong & Steiner, P.C.

(57) ABSTRACT

A method and apparatus for detecting changes in the vibrational mode spectra and/or elasticity of a pellicle without reliance upon visual inspection are provided. Embodiments include providing a pellicle, a lower surface of the pellicle attached to a photomask; directing light from a light source onto an upper surface of the pellicle at an angle to the upper surface; causing a deflection of the pellicle concurrently with the light being directed onto the pellicle; detecting light reflected off of the deflected pellicle; and characterizing a vibrational mode of the pellicle based on the detection.

6 Claims, 7 Drawing Sheets

IN-SITU CONTACTLESS MONITORING OF PHOTOMASK PELLICLE DEGRADATION

TECHNICAL FIELD

The present disclosure relates to semiconductor device lithography processes. The present disclosure is particularly applicable to detecting pellicle degradation.

BACKGROUND

A known approach for monitoring pellicle degradation involves visual inspection of the pellicle to detect cracks at its attachment to a photomask and/or unwanted material aggregation on the pellicle. However, a visual inspection can lack the precision required to generate reliable results and often occurs after the fact, preventing right-in-time repelling.

A need therefore exists for methodology and an apparatus enabling in-situ contactless pellicle degradation monitoring that is independent of visual inspection.

SUMMARY

An aspect of the present disclosure is a method of detecting changes in the vibrational mode spectra and/or elasticity of a pellicle without reliance upon visual inspection.

Another aspect of the present disclosure is an apparatus enabling non-visual detection of changes in the vibrational mode spectra and/or elasticity of a pellicle.

Additional aspects and other features of the present disclosure will be set forth in the description which follows and in part will be apparent to those having ordinary skill in the art upon examination of the following or may be learned from the practice of the present disclosure. The advantages of the present disclosure may be realized and obtained as particularly pointed out in the appended claims.

According to the present disclosure, some technical effects may be achieved in part by a method including: providing a pellicle, a lower surface of the pellicle attached to a photomask; directing light from a light source onto an upper surface of the pellicle at an angle to the upper surface; causing a deflection of the pellicle concurrently with the light being directed onto the pellicle; detecting light reflected off of the deflected pellicle; and characterizing a vibrational mode of the pellicle based on the detection.

Aspects of the present disclosure include causing the deflection by: generating a frequency-swept acoustic wave with a frequency generator, and directing the frequency-swept acoustic wave at the pellicle via a loudspeaker; and characterizing the vibrational mode of the pellicle based on a spectral analysis. Other aspects include placing the pellicle in a pressure chamber prior to directing the frequency-swept acoustic wave at the pellicle; and reducing an air pressure in the pressure chamber prior to detecting the reflected light. Further aspects include moving the light source and a photodetector for detecting the light in tandem in-plane relative to the pellicle; and characterizing the vibrational mode of the pellicle based on an amplitude measurement. Additional aspects include causing the deflection by: generating a frequency-swept acoustic wave with a frequency generator; and directing the frequency-swept acoustic wave at the pellicle via a loudspeaker. Another aspect includes causing the deflection by: generating a frequency-swept acoustic wave with a frequency generator; directing the frequency-swept acoustic wave at the pellicle via a loudspeaker; and moving the loudspeaker in tandem with the light source and the photodetector in-plane relative to the pellicle concurrently with directing the frequency-swept acoustic wave at the pellicle. Other aspects include causing the deflection by: directing air at the upper surface of the pellicle from above the pellicle via an air nozzle; and moving the air nozzle in tandem with the light source and the photodetector in-plane relative to the pellicle concurrently with directing the air at the pellicle. Further aspects include causing the deflection by: placing the pellicle in a pressure chamber; and maintaining a constant pressure delta between pressure in the pressure chamber and pressure between the pellicle and the photomask concurrently with detecting the light by compensating for air flowing through a pellicle vent from between the pellicle and the photomask to the pressure chamber. Additional aspects include causing the deflection by: placing the pellicle in a pressure chamber; changing a pressure of the pressure chamber; and detecting the light fast enough to neglect air flowing through a pellicle vent from between the pellicle and the photomask to the pressure chamber. Another aspect includes detecting a degradation of the pellicle based on the vibrational mode of the pellicle.

Another aspect of the present disclosure is an apparatus including: an opaque molybdenum silicide (MoSi) on glass (OMOG) photomask; a supporting frame formed on an upper surface of the photomask, the supporting frame having a pellicle vent; a pellicle attached to the supporting frame; a light source; a means for deflecting the pellicle; a photodetector for detecting a light from the light source directed at and reflected off of an upper surface of the pellicle concurrently with a deflection of the pellicle; a means for analyzing detected light.

Aspects of the apparatus include the means for deflecting and analyzing including a frequency generator, a loudspeaker, and a spectral analysis module. Other aspects include the loudspeaker being directed at the pellicle to cause the deflection of the pellicle. Further aspects include a pressure chamber wherein the photomask, the supporting frame, the pellicle, and the loudspeaker are placed in the pressure chamber, and an air pressure of the pressure chamber being reduced prior to deflection of the pellicle by the loudspeaker. Additional aspects include the means for deflecting and analyzing including a frequency generator, a loudspeaker, and an amplitude measurement module. Another aspect includes the loudspeaker being directed at the pellicle. Other aspects include the loudspeaker being directed at the pellicle and the light source, the photodetector, and the loudspeaker are caused to move in tandem in-plane relative to the pellicle to generate a localized pellicle deflection and a spatially resolved measurement of the localized pellicle deflection. Further aspects include the means for deflecting and analyzing including an air nozzle and an amplitude measurement module, the air nozzle being directed at the upper surface of the pellicle from above the pellicle, and wherein the light source, the photodetector, and the air nozzle are caused to move in tandem in-plane relative to the pellicle to generate a localized pellicle deflection and a spatially resolved measurement of the localized pellicle deflection.

A further aspect of the present disclosure is a method including: providing a pellicle, a lower surface of the pellicle attached to a photomask; directing a light from a light source onto the upper surface of the pellicle from above the pellicle, the light source being stationary or movable in-plane relative to the pellicle; generating a frequency-swept acoustic wave with a frequency generator; directing the frequency-swept acoustic wave at the pellicle via a loudspeaker concurrently with the light source being directed onto the pellicle; detecting light reflected off of the upper surface of the pellicle with a photodetector, the photodetector being stationary or movable in tandem with the light source in-plane relative to the pellicle; characterizing a vibrational mode of the pellicle based on a spectral analysis or an amplitude measurement of detected light; and detecting a degradation of the pellicle based on the vibrational mode of the pellicle.

Additional aspects and technical effects of the present disclosure will become readily apparent to those skilled in the art from the following detailed description wherein embodiments of the present disclosure are described simply by way of illustration of the best mode contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF THE DRAWINGS

The present disclosure is illustrated by way of example, and not by way of limitation, in the figures of the accompanying drawing and in which like reference numerals refer to similar elements and in which.

DETAILED DESCRIPTION

In the following description, for the purposes of explanation, numerous specific details are set forth in order to provide a thorough understanding of exemplary embodiments. It should be apparent, however, that exemplary embodiments may be practiced without these specific details or with an equivalent arrangement. In other instances, well-known structures and devices are shown in block diagram form in order to avoid unnecessarily obscuring exemplary embodiments. In addition, unless otherwise indicated, all numbers expressing quantities, ratios, and numerical properties of ingredients, reaction conditions, and so forth used in the specification and claims are to be understood as being modified in all instances by the term "about."

The present disclosure addresses and solves the current problems of a lack of precision and an inability for right-in-time repelling attendant upon visually monitoring a photomask's pellicle degradation.

Methodology in accordance with embodiments of the present disclosure includes providing a pellicle, a lower surface of the pellicle attached to a photomask. Light is directed from a light source onto an upper surface of the pellicle at an angle to the upper surface. A deflection of the pellicle is caused concurrently with the light being directed onto the pellicle. Light reflected off of the deflected pellicle is detected and a vibrational mode of the pellicle is characterized based on the detection.

Still other aspects, features, and technical effects will be readily apparent to those skilled in this art from the following detailed description, wherein preferred embodiments are shown and described, simply by way of illustration of the best mode contemplated. The disclosure is capable of other and different embodiments, and its several details are capable of modifications in various obvious respects. Accordingly, the drawings and description are to be regarded as illustrative in nature, and not as restrictive.

Figure 1:
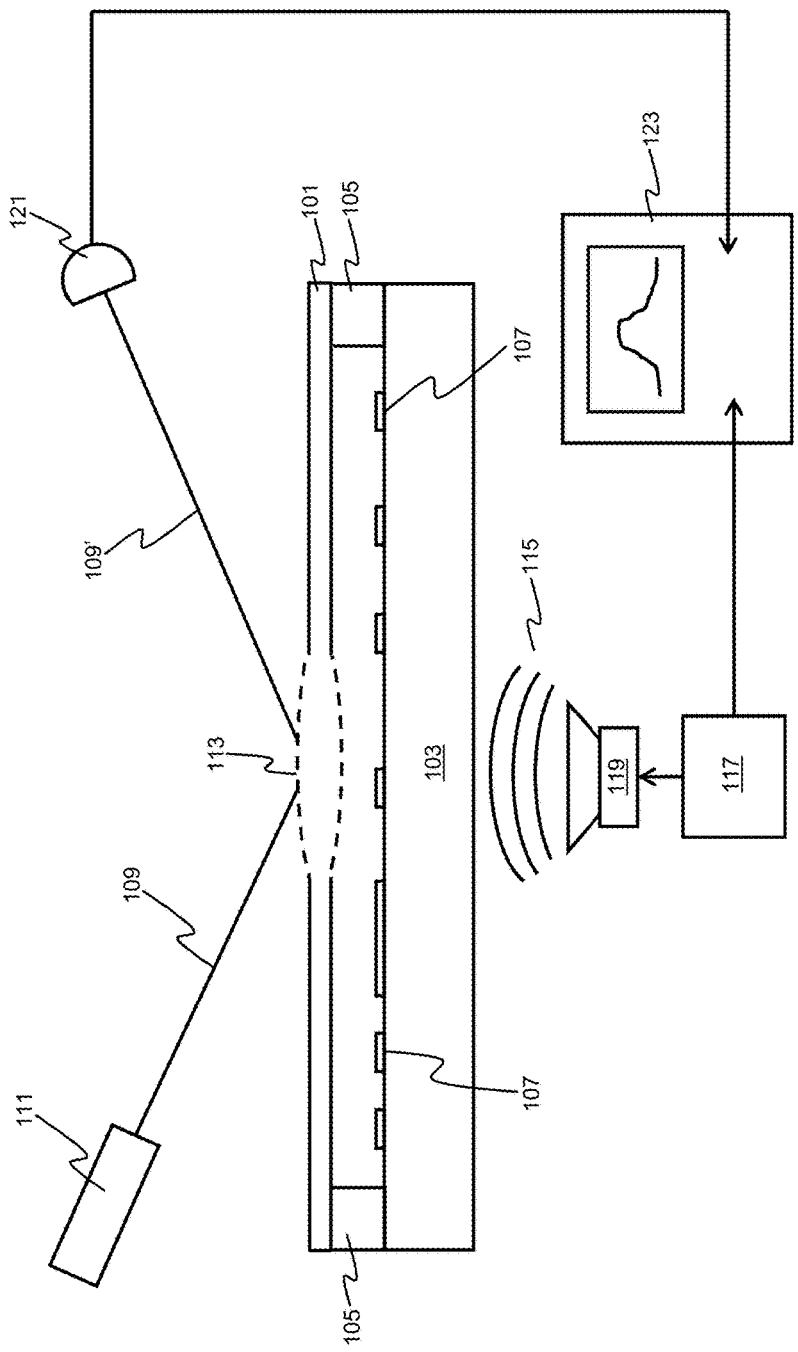
FIG. 1 schematically illustrates an in-situ contactless monitoring of a photomask's pellicle degradation based on a frequency-swept acoustic wave directed at the pellicle and a spectral analysis, in accordance with an exemplary embodiment.
Figure 2A:
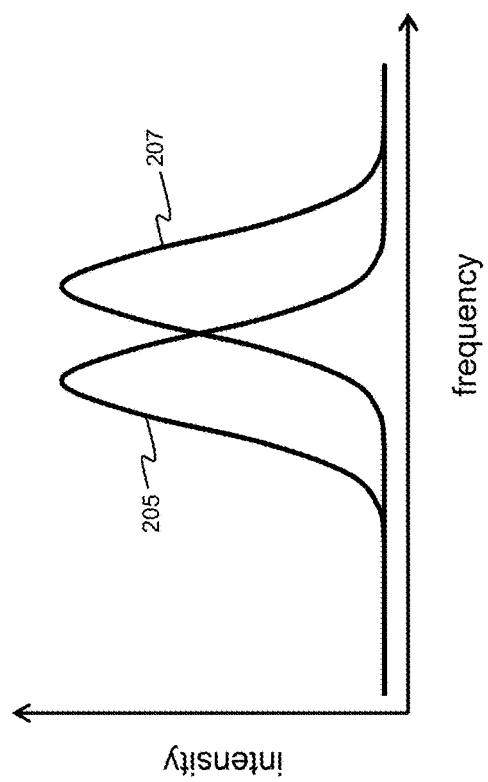
FIGS. 2A and 2B are example results of an in-situ contactless monitoring of a photomask's pellicle degradation, in accordance with an exemplary embodiment.

FIG. 1 (a cross-sectional view) schematically illustrates an in-situ contactless monitoring of a photomask's pellicle degradation based on a frequency-swept acoustic wave directed at the pellicle and a spectral analysis, e.g., using a network analyzer, in accordance with an exemplary embodiment. Adverting to FIG. 1, a pellicle 101 is attached to a photomask 103 with a supporting frame 105, e.g., similar to a drum skin. The photomask 103 may be constructed, for example, of translucent glass and include an opaque MoSi layer 107 on the upper surface of the photomask 103, e.g., an OMOG photomask. The light 109, e.g., laser light, is directed from a light source 111, e.g., a laser, onto the upper surface of the pellicle 101 at an angle to the upper surface. A deflection of the pellicle 101, as depicted by the dashed lines 113, is caused concurrently with the light 109 being directed onto the pellicle 101. In this example, the deflection is caused by a frequency-swept acoustic wave 115 generated by a frequency generator 117 and directed at the pellicle 101 via a loudspeaker 119. Although shown below the photomask 103, the loudspeaker 119 may be positioned in any number of ways relative to the photomask 103 and the pellicle 101 to direct a frequency-swept acoustic wave at the pellicle 101. The light 109' reflected off of the deflected pellicle 101 is detected by a photodetector or photodiode 121, e.g., a quadrant photodiode. In this example, the frequency generator 117 and the photodetector 121 are connected to a spectral analysis module 123, e.g., a network analyzer. The spectral analysis module 123 may be used, for example, to characterize the vibrational mode and/or elasticity of the pellicle 101 based on the detection of the reflected light 109' by the photodetector 121. In the case of a crack in the supporting frame 105, the spectral width of the monitored mode will increase and, therefore, make it detectable, as depicted in FIG. 2A. Likewise, in the case of an aggregation of unwanted material on the pellicle 101, the central frequency of the monitored mode will change and, therefore, make it detectable, as depicted in FIG. 2B.

Figure 2B:
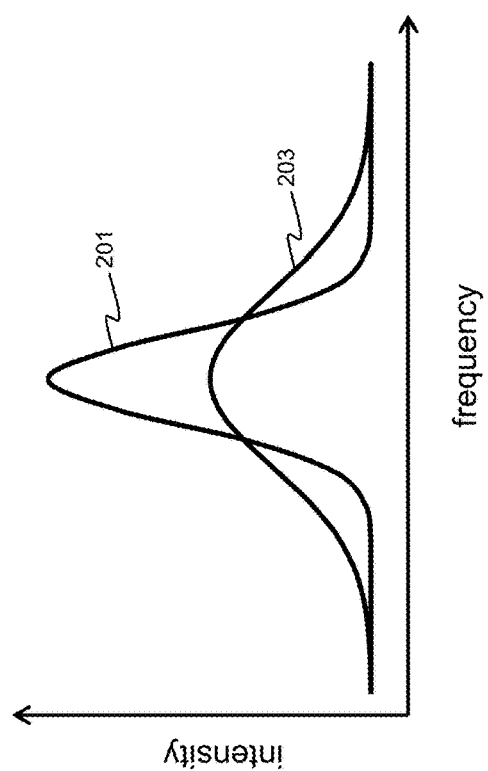

FIGS. 2A and 2B are example spectral analysis results of an in-situ contactless monitoring of a photomask's pellicle degradation, in accordance with an exemplary embodiment. FIG. 2A represents the different spectral analysis results of a non-partially detached pellicle, as depicted by the line 201, and a partially detached pellicle, as depicted by the line 203. As a result of the crack in the attachment of the pellicle, the spectral width of the monitored mode increases and, therefore, becomes detectable. FIG. 2B represents the different spectral analysis results of a clean pellicle, as depicted by the line 205, and an aggregated pellicle, e.g. where unwanted material has aggregated on the pellicle, as depicted by the line 207. As a result, because of the unwanted material on the pellicle, the central frequency of the monitored mode will change and, therefore, become detectable.

Figure 3:
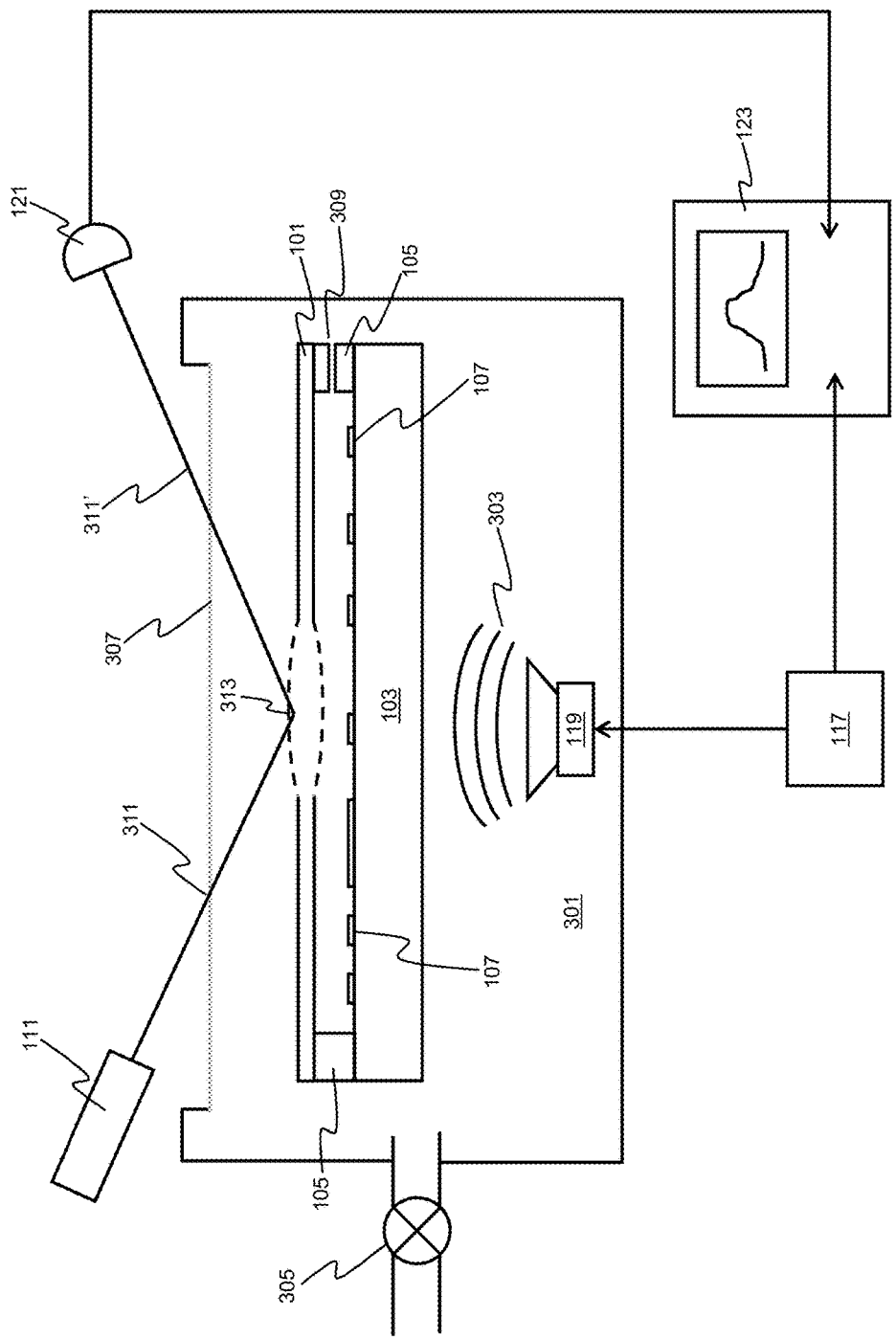
FIG. 3 schematically illustrates an in-situ contactless monitoring of a photomask's pellicle degradation based on a frequency-swept acoustic wave directed at the pellicle under reduced pressure and a spectral analysis, in accordance with an exemplary embodiment.

Adverting to FIG. 3, an in-situ contactless monitoring of a photomask's pellicle degradation is schematically illustrated based on a frequency-swept acoustic wave directed at the pellicle similar to FIG. 1; however, the pellicle 101, the photomask 103, the supporting frame 105, and the loudspeaker 119 are placed in a pressure chamber 301 prior to directing the frequency-swept acoustic wave 303 at the pellicle 101. Again, although shown below the photomask 103, the loudspeaker 119 may be positioned within the pressure chamber 301 in any number of ways relative to the photomask 103 and the pellicle 101 to direct a frequency-swept acoustic wave at the pellicle 101. The pressure chamber 301 includes a pressure control 305 and a window 307, e.g., an anti-reflection (AR) window. In this example, the supporting frame 105 also includes a pellicle vent 309. The light 311, e.g., laser light, is directed from the light source 111, e.g., a laser, onto the upper surface of the pellicle 101 at an angle to the upper surface. A deflection of the pellicle 101 is then caused concurrently with the light 311 being directed onto the pellicle 101, as depicted by the dashed lines 313. In this example, the deflection is again caused by a frequency-swept acoustic wave 303 generated by the frequency generator 117 and directed at the pellicle 101 from below the photomask 103 by the loudspeaker 119. In this example, the air pressure inside of the pressure chamber 301 is reduced prior to the photodetector or photodiode 121, e.g., a quadrant photodiode, detecting the light 311' reflected off of the deflected pellicle 101. The frequency generator 117 and the photodetector 121 are again connected to a spectral analysis module 123, e.g., a network analyzer module 123, and the spectral analysis module 123 may be used, for example, to characterize the vibrational mode and/or elasticity of the pellicle 101 under reduced pressure based on the detection of the reflected light 311' by the photodetector 121. The reduced attenuation by air enables a more sensitive spectral analysis. However, the pressure change must be slow enough to allow equilibration through the pellicle vent 309.

Figure 4:
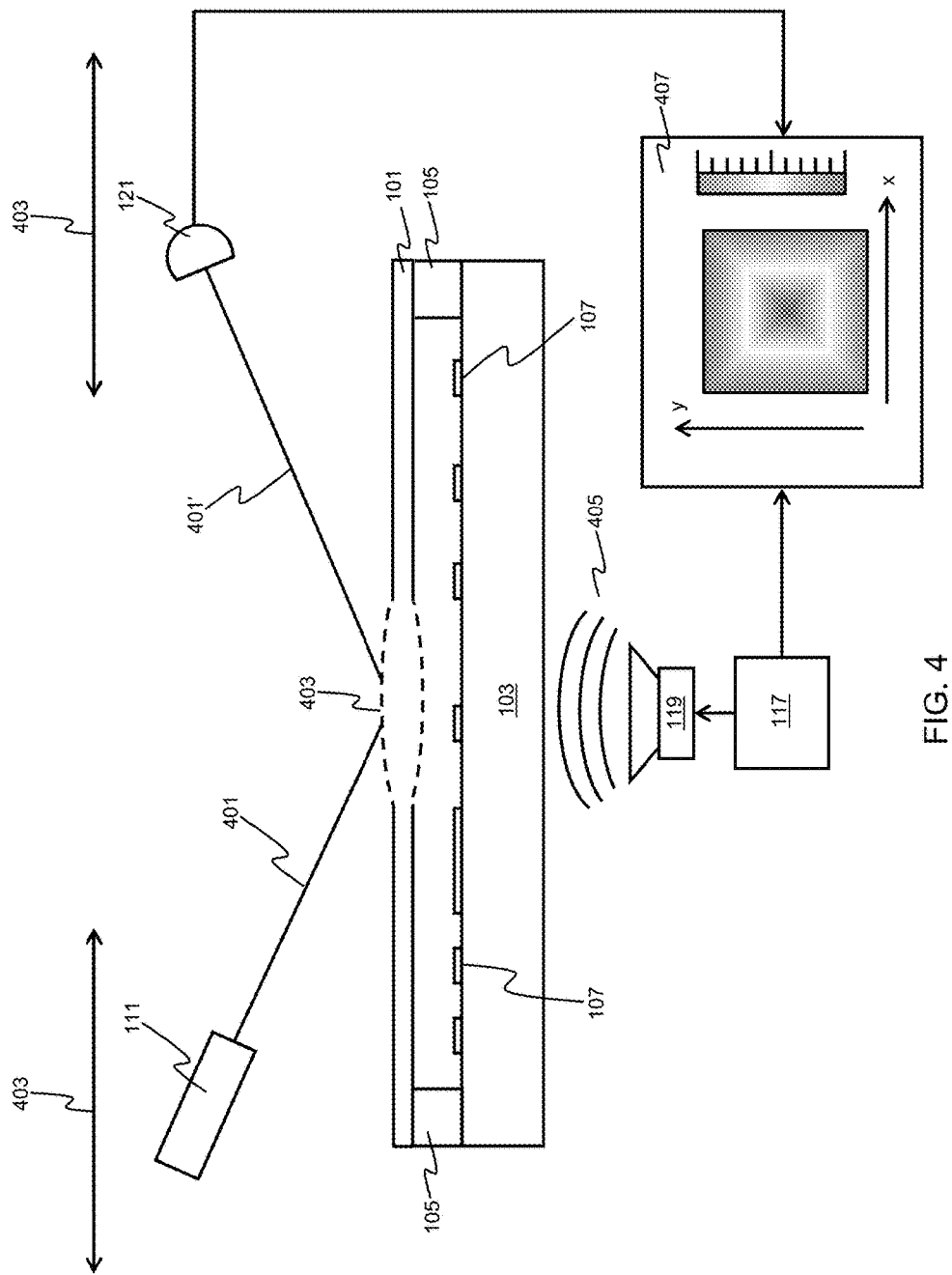
FIG. 4 schematically illustrates an in-situ contactless monitoring of a photomask's pellicle degradation based on a frequency-swept acoustic wave directed at the pellicle and an amplitude measurement, in accordance with an exemplary embodiment.

FIG. 4 schematically illustrates an in-situ contactless monitoring of a photomask's pellicle degradation based on a frequency-swept wave directed at the pellicle similar to FIG. 1; however, the light source 111 and the photodetector 121 may move in-plane relative to the pellicle 101 as depicted by the arrows 403 to generate a spatially resolved measurement of the pellicle's elasticity. The light source 111 and the photodetector 121 may be moved, for example, by a linear positioner, e.g., an electrical stepper motor. For example, the light 401, e.g., laser light, is directed from the light source 111, e.g., a laser, onto the upper surface of the pellicle 101 at an angle to the upper surface. A deflection of the pellicle 101, as depicted by the dashed lines 403, is then caused concurrently with the light 401 being directed onto the pellicle 101. While the deflection of the pellicle 101 is ongoing, the light source 111 and the photodetector 121 may be moved in-plane relative to the pellicle 101. In this example, the deflection of the pellicle 101 is again caused by a frequency-swept acoustic wave 405 generated by the frequency generator 117 and directed at the pellicle 101 via the loudspeaker 119. Again, although shown below the photomask 103, the loudspeaker 119 may be positioned in any number of ways relative to the photomask 103 and the pellicle 101 to direct a frequency-swept acoustic wave at the pellicle 101. In this example, the frequency generator 117 and the photodetector 121 are connected to an amplitude measurement module 407 and the amplitude measurement module 407 may be used, for example, to characterize the vibrational mode and/or elasticity of the pellicle 101, e.g., by generating spatially resolved measurements of the pellicle 101's elasticity, based on the detection of the reflected light 401' by the photodetector 121.

Figure 5:
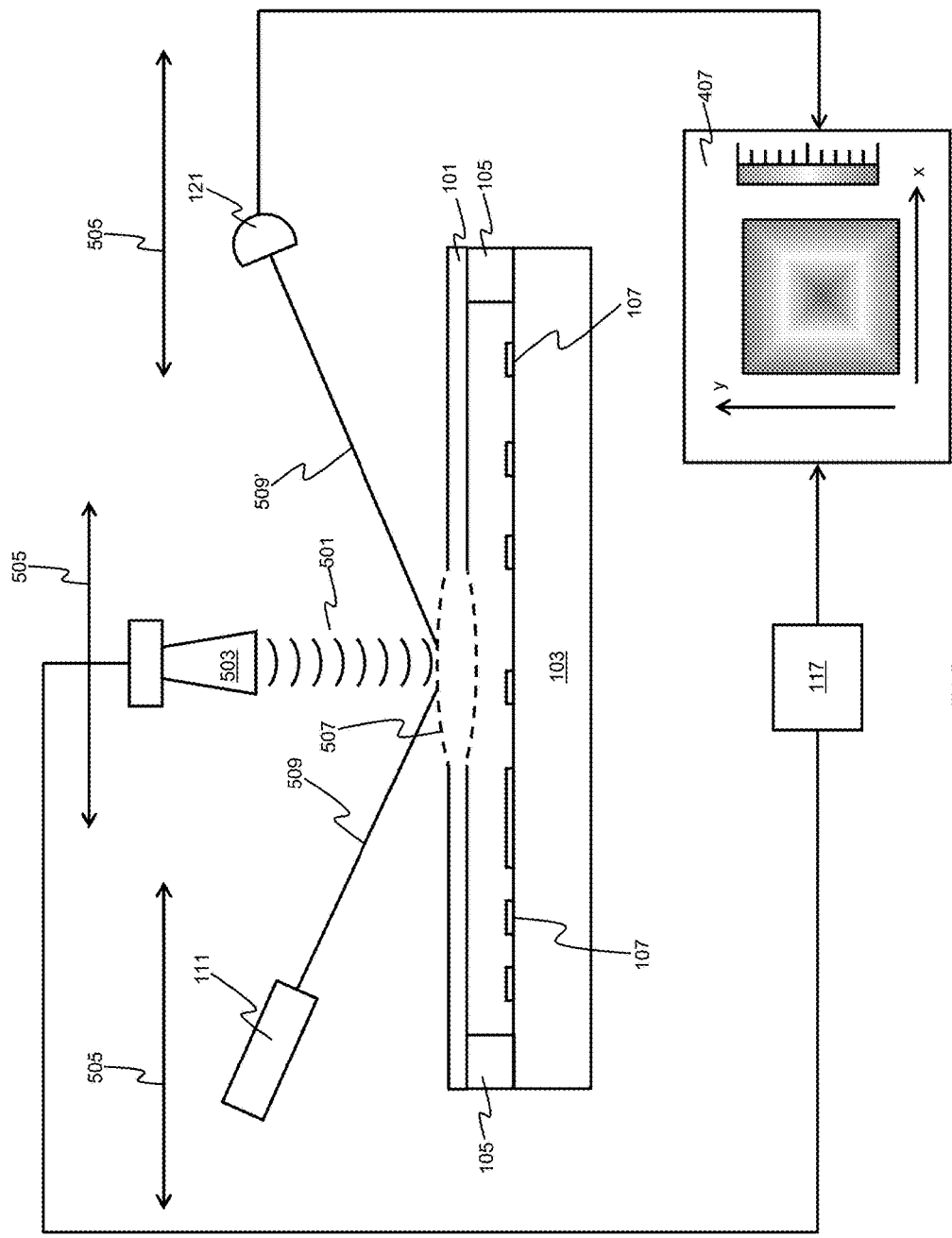
FIG. 5 schematically illustrates an in-situ contactless monitoring of a photomask's pellicle degradation based on a frequency-swept acoustic wave directed at the pellicle from above the pellicle and an amplitude measurement, in accordance with an exemplary embodiment.

Adverting to FIG. 5, an example in-situ contactless monitoring of a photomask's pellicle degradation is schematically illustrated based on a frequency-swept wave directed at the pellicle similar to FIG. 4; however, the frequency-swept wave 501 is directed at the upper surface of the pellicle 101 from above the pellicle 101 via the loudspeaker 503. The loudspeaker 503 can be moved, for example, in tandem with the light source 111 and the photodetector 121 in-plane relative to the pellicle 101, as depicted by the arrows 505, concurrently with directing the frequency-swept acoustic wave 501 at the pellicle 101. As a result, deflections of the pellicle 101, as depicted by the dashed lines 507, are caused concurrently with the light 509 being directed onto the pellicle 101. The amplitude measurement module 407 may again be used, for example, to characterize the vibrational mode and/or elasticity of the pellicle 101, e.g., by generating spatially resolved measurements of the pellicle 101's elasticity, based on the detection of the reflected light 509' by the photodetector 121.

Figure 6:
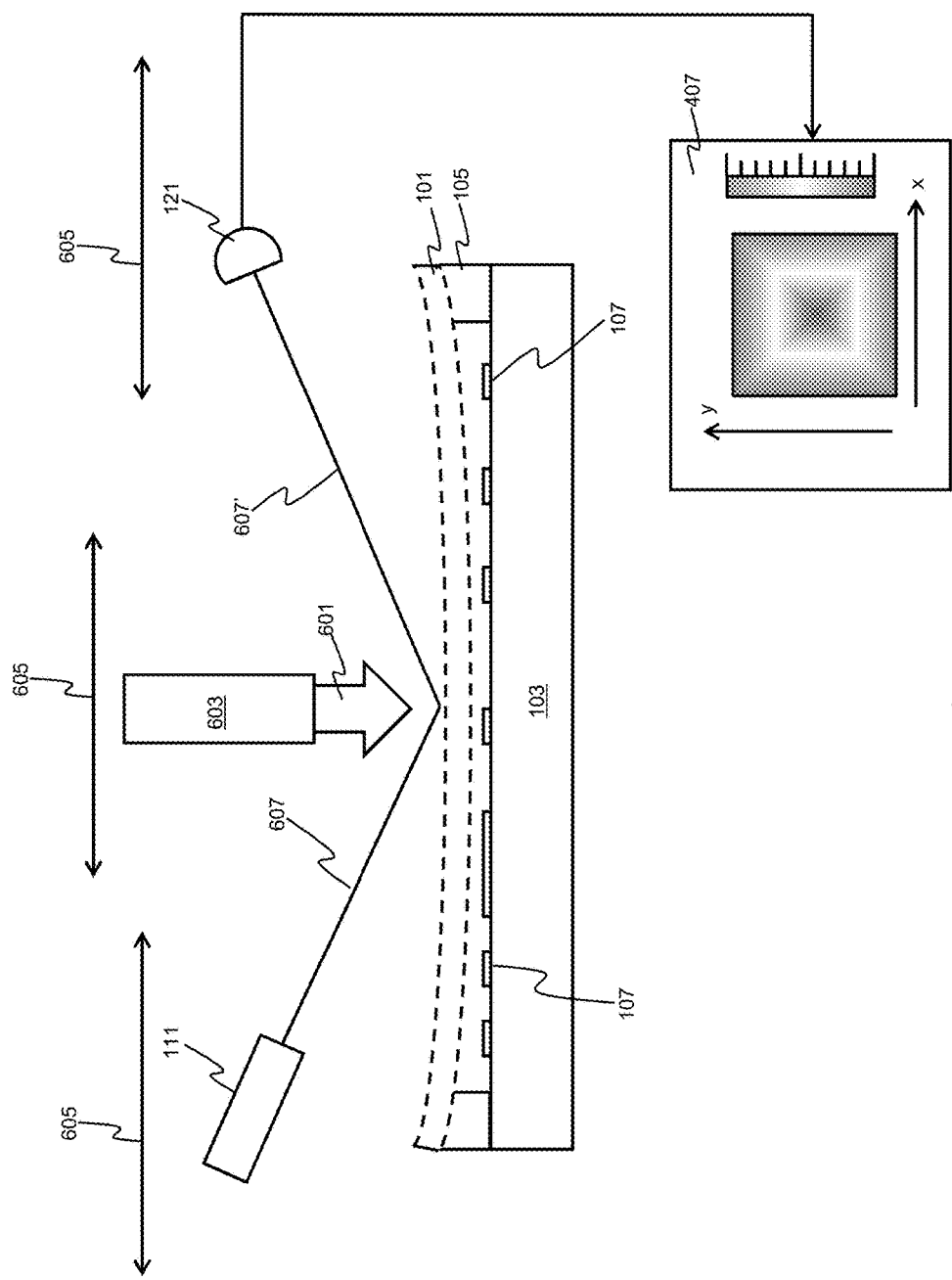
FIG. 6 schematically illustrates an in-situ contactless monitoring of a photomask's pellicle degradation based on directing air at the pellicle from above the pellicle and an amplitude measurement, in accordance with an exemplary embodiment.

FIG. 6 schematically illustrates an example in-situ contactless monitoring of a photomask's pellicle degradation similar to FIG. 5; however, the deflection of the pellicle 101 is based on directing air 601 at the upper surface of the pellicle 101 from above the pellicle 101 via an air nozzle 603, as depicted by the curved dashed lines of the pellicle 101. Similar to the loudspeaker 503 in FIG. 5, the air nozzle 603 can move, for example, in tandem with the light source 111 and the photodetector 121 in-plane relative to the pellicle 101, as depicted by the arrows 605, concurrently with directing air 601 at the pellicle 101. Consequently, deflections of the pellicle 101, as depicted by the curved dashed lines of the pellicle 101, are caused concurrently with the light 607 being directed onto the pellicle 101. The amplitude measurement module 407 may again be used, for example, to characterize the vibrational mode and/or elasticity of the pellicle 101, e.g., by generating spatially resolved measurements of the pellicle 101's elasticity, based on the detection of the reflected light 607' by the photodetector 121.

Figure 7:
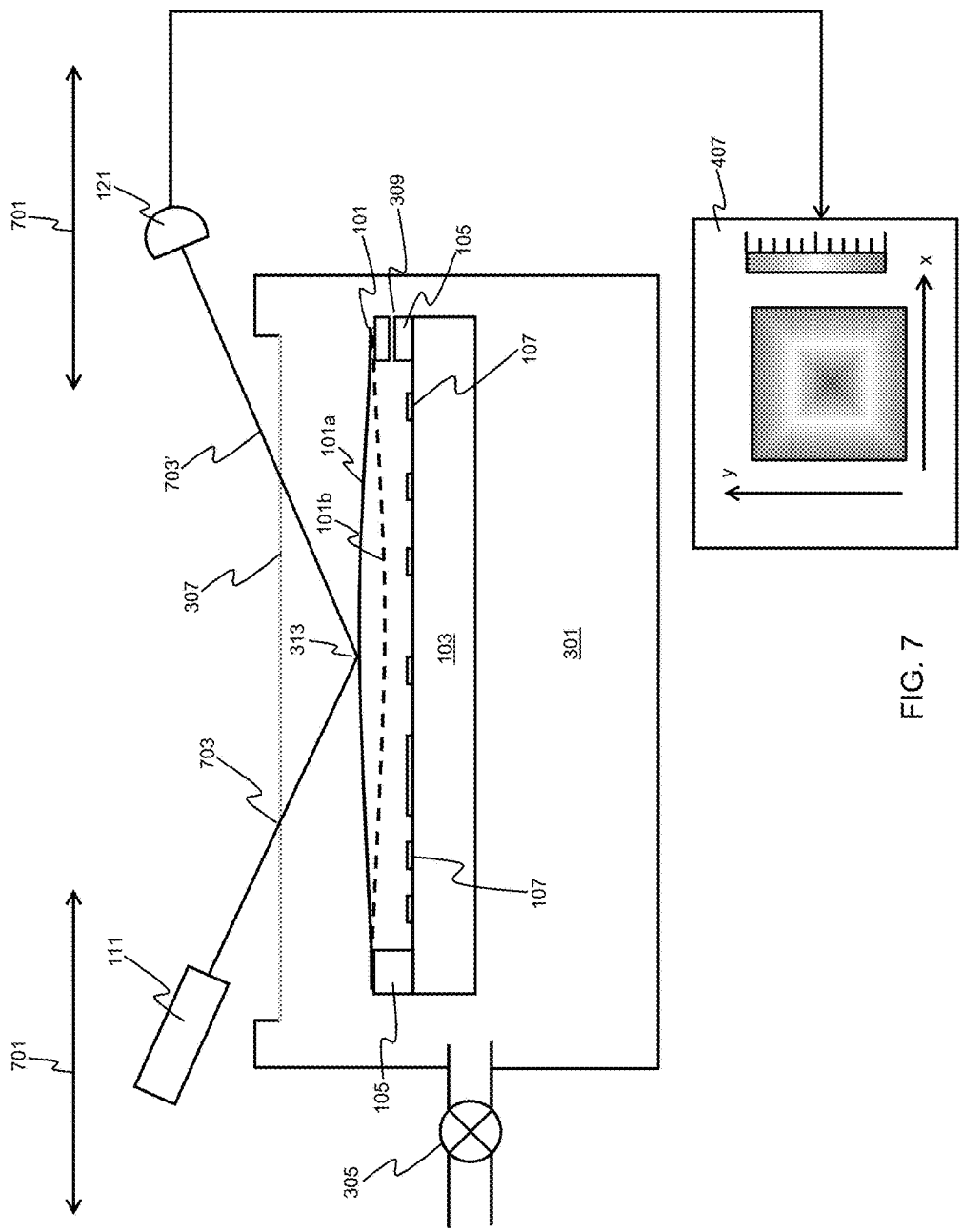
FIG. 7 schematically illustrates an in-situ contactless monitoring of a photomask's pellicle degradation based on pellicle deflection by over or under pressure and an amplitude measurement, in accordance with an exemplary embodiment.

Adverting to FIG. 7, an in-situ contactless monitoring of a photomask's pellicle degradation is schematically illustrated based on pellicle deflection by over or under pressure. Similar to FIG. 3, the pellicle 101, the photomask 103, the supporting frame 105, and the loudspeaker 119 are placed in a pressure chamber 301 prior to deflecting the pellicle 101. Again, the pressure chamber 301 includes a pressure control 305 and a window 307, e.g., an AR window, and the supporting frame 105 includes a pellicle vent 309. In this example, similar to FIG. 4, the light source 111 and the photodetector 121 may move in-plane relative to the pellicle 101 as depicted by the arrows 701. The light 703, e.g., laser light, is directed from the light source 111, e.g., a laser, onto the upper surface of the pellicle 101 through the window 307 at an angle to the upper surface. Deflections of the pellicle 101 may be caused concurrently with the light 703 being directed onto the pellicle 101 and light 703' being detected, for example, by maintaining a constant pressure delta between pressure in the pressure chamber 301 and pressure between the pellicle 101 and the photomask 103. The pressure delta may be maintained by compensating for air flowing through the pellicle vent 309 from between the pellicle 101 and the photomask 103 to the pressure chamber 301. Alternatively, the pellicle 101 may be deflected, for example, by changing the pressure of the pressure chamber 301 and detecting the reflected light 703' fast enough to neglect air flowing through the pellicle vent 309 from between pellicle 101 and the photomask 103 to the pressure chamber 301. The deflection variants of the pellicle 101 are depicted by the lines 101a and 101b of the pellicle 101. While either variant of the deflections of the pellicle 101 is ongoing, the light source 111 and the photodetector 121 may be moved, for example, in-plane relative to the pellicle 101. The amplitude measurement module 407 may then be used, for example, to characterize the vibrational mode and/or elasticity of the pellicle 101, e.g., by generating spatially resolved measurements of the pellicle 101's elasticity, based on the detection of the reflected light 703' by the photodetector 121.

The embodiments of the present disclosure can achieve several technical effects including detecting changes in the vibrational mode spectra and/or elasticity of the pellicle that indicate that the pellicle is close to failure or contaminated without reliance on visual inspection. In addition, the process can be integrated into any fab environment, e.g., reticle stocker, scanner, etc., and the process is non-destructive for both the photomask and the pellicle. Embodiments of the present disclosure enjoy utility in various industrial applications as, for example, microprocessors, smart phones, mobile phones, cellular handsets, set-top boxes, DVD recorders and players, gaming systems, and digital cameras. The present disclosure therefore enjoys industrial applicability in any of various types of highly integrated semiconductor devices formed by lithography.

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. A method comprising:
   providing a pellicle, a lower surface of the pellicle attached to a photomask;
   directing light from a light source onto an upper surface of the pellicle at an angle to the upper surface;
   causing a deflection of the pellicle concurrently with the light being directed onto the pellicle by:
      generating a frequency-swept acoustic wave with a frequency generator;
      directing the frequency-swept acoustic wave at the pellicle via a loudspeaker;
      moving the light source and a photodetector for detecting the light in tandem in-plane relative to the pellicle; and
      moving the loudspeaker in tandem with the light source and the photodetector in-plane relative to the pellicle concurrently with directing the frequency-swept acoustic wave at the pellicle, the photodetector configured to detect light from the light source;
   detecting light reflected off of the deflected pellicle by the photodetector; and
   characterizing a vibrational mode of the pellicle based on an amplitude measurement of the detected light.

2. The method according to claim 1, comprising:
   placing the pellicle in a pressure chamber prior to directing the frequency-swept acoustic wave at the pellicle; and
   reducing an air pressure in the pressure chamber prior to detecting the reflected light.

3. The method according to claim 1, further comprising detecting a degradation of the pellicle based on the vibrational mode of the pellicle.

4. An apparatus comprising:
   an opaque molybdenum silicide (MoSi) on glass (OMOG) photomask;
   a supporting frame formed on an upper surface of the photomask, the supporting frame having a pellicle vent;
   a pellicle attached to the supporting frame;
   a light source;
   a means for deflecting the pellicle, wherein the means for deflecting comprises a frequency generator and a loudspeaker;
   a photodetector for detecting a light from the light source directed at and reflected off of an upper surface of the pellicle concurrently with a deflection of the pellicle; and
   a means for analyzing detected light, wherein the means for analyzing comprises an amplitude measurement module to characterize a vibrational mode of the pellicle,
   wherein the loudspeaker is directed at the pellicle, and wherein the light source, the photodetector and the loudspeaker are caused to move in-plane relative to the pellicle to generate a localized pellicle deflection and a spatially resolved measurement of the localized pellicle deflection by the amplitude measurement module.

5. The apparatus according to claim 4, further comprising a pressure chamber wherein the photomask, the supporting frame, the pellicle, and the loudspeaker are placed in the pressure chamber, and an air pressure of the pressure chamber is reduced prior to deflection of the pellicle by the loudspeaker.

6. A method comprising:
   providing a pellicle, a lower surface of the pellicle attached to a photomask;
   directing light from a light source onto an upper surface of the pellicle at an angle to the upper surface;
   causing a deflection of the pellicle concurrently with the light being directed onto the pellicle by:
      directing air at the upper surface of the pellicle from above the pellicle via an air nozzle;
      moving the light source and a photodetector for detecting the light in tandem in-plane relative to the pellicle; and
      moving the air nozzle in tandem with the light source and the photodetector in-plane relative to the pellicle concurrently with directing the air at the pellicle, the photodetector configured to detect light from the light source;
detecting light reflected off of the deflected pellicle by the photodetector; and
characterizing a vibrational mode of the pellicle based on an amplitude measurement of the detected light.

\* \* \* \* \*